United States Patent [19]

Baglioni

[11] Patent Number: 4,652,575

[45] Date of Patent: Mar. 24, 1987

[54] 2-(ETHYLENE-THIO METHYL FURANYL)AMINO THIAZOLE DERIVATIVES HAVING ACID SECRETION INHIBITING ACTIVITY

[75] Inventor: Alessandro Baglioni, Rome, Italy

[73] Assignee: Medosan Industrie Biochimiche Riunite S.p.A., Albano Laziale, Italy

[21] Appl. No.: 775,245

[22] Filed: Sep. 12, 1985

[30] Foreign Application Priority Data

Oct. 5, 1984 [IT] Italy ................................. 48956 A/84

[51] Int. Cl.$^4$ .................... A61K 31/425; C07D 417/12
[52] U.S. Cl. ..................................... 514/370; 548/193; 549/495
[58] Field of Search ......................... 548/193; 514/370

[56] References Cited

U.S. PATENT DOCUMENTS 4,521,418  6/1985  Brown et al. ......................... 548/193
4,525,477  6/1985  Roantree et al. .................... 548/193

FOREIGN PATENT DOCUMENTS 4825499  12/1970  Japan ..................................... 514/370

*Primary Examiner*—Donald G. Daus
*Assistant Examiner*—Stephen M. Kapner
*Attorney, Agent, or Firm*—Cushman, Darby & Cushman

[57] ABSTRACT

Compound of formula (I)

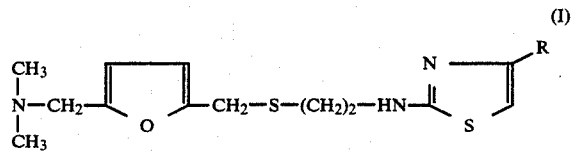

wherein R is an alkyl or an aromatic group, having pharmaceutical utility as an agent for treating a condition mediated through gastric acid secretion for reducing the volume and the acidity of gastric juice.

8 Claims, No Drawings

2-(ETHYLENE-THIO METHYL FURANYL)AMINO THIAZOLE DERIVATIVES HAVING ACID SECRETION INHIBITING ACTIVITY

DISCLOSURE

BACKGROUND OF THE INVENTION

1. Field of the Invention

The present invention relates to new derivatives of 2-amino-thiazole having a selective inhibitory activity on histamine receptors, a method of preparation thereof, pharmaceutical compositions and their use as therapeutic agents.

2. Description of the Prior Art

It is known that the histamine receptors are divided into $H_1$ and $H_2$ receptors (Ash and Child, Brit. J. Pharmacol., Chemother, 1966, 27, 427 and Black et al, Nature, 1972, 236, 385) and that the gastric secretion, in particular, is mediated by $H_2$ receptors.

It is generally recognized that the $H_2$ receptor antagonists are efficaceous inhibitors of the gastric acid secretion as shown in experimental tests on animals (rat and dog) and on humans (Brimblecomble, J. Int. Med. Res. 3, 86 (1975)).

It is additionally known that the $H_2$ antagonists, such as Burimamide, Metiamide, Cimetidine, Ranitidine are effective to reduce the gastric acid secretion in experimental tests on animals, as well as on humans. The $H_2$ antagonists can consequently be used in the treatment of conditions resulting in a gastric acid secretion excess, such as in peptic and gastric ulcer.

SUMMARY OF THE INVENTION

It has been found that several derivatives of 2-amino-thiazole antagonize the $H_2$ receptors and they inhibit the gastric acid secretion. The experimental methods used to show said activity are described hereinafter.

Object of the invention are compounds having a therapeutic utility, of the general formula (I)

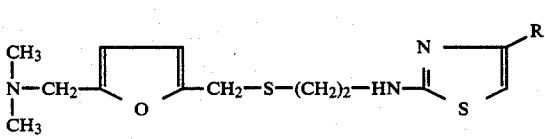
(I)

wherein R represents a $C_1$–$C_6$ alkyl group, naphthyl, adamantyl, a diphenyl ether group, phenyl, or a substituted phenyl, the substituent being halogen, preferably bromine, inf.alkoxy, preferably methoxy, inf.alkylaryl, preferably methyl-biphenyl, styryl, phenoxy or phenyl.

The invention also includes the physiologic salts, hydrates, N- and S-oxides and tautomers of the compounds of formula (I).

Additional objects of the invention are pharmaceutical compositions comprising as an active substance for the inhibition of the gastric secretion, a compound of formula (I).

The general method for the preparation of compounds of formula (I) is described by the following scheme:

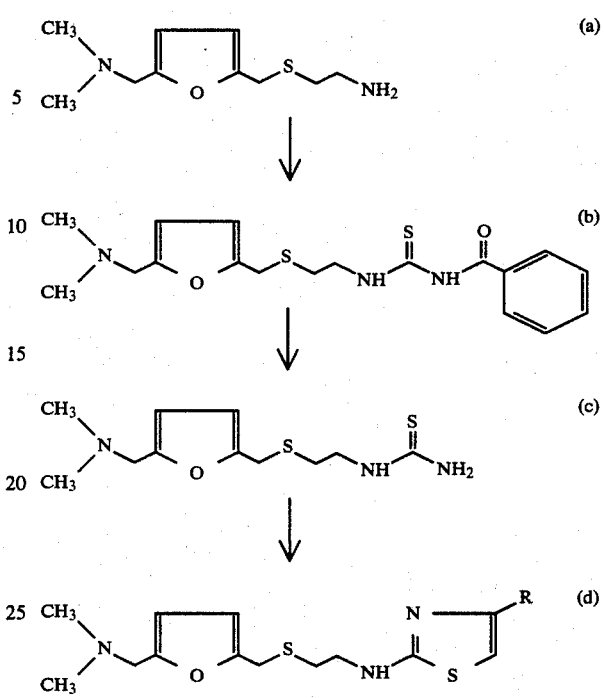

Compound (a) is prepared in a conventional way as described, for example, in Belgian Pat. No. 857388, Belgian Pat. No. 885089, U.S. Pat. No. 4,128,658.

Compound (a) reacts with a compound able to form the group

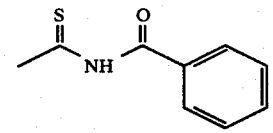

Treating the compound (b) so obtained under basic conditions, gives the compound (c). By reacting the compound (c) under suitable conditions with a substituted ω-halocarbonyl compound of general formula:

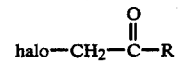

the compounds of general formula (I) are obtained, R having the meaning previously recited.

Compound (b) moreover shows useful therapeutic properties, in that it is an antagonist of the histamine $H_2$ receptors and reduces gastric secretion.

Examples 1 to 13 show the preparation of the compounds of formula (I) and the intermediates thereof.

EXAMPLE 1

N-benzoyl-N'-(2-(((5-(dimethylamino)methyl-2-furanyl)methyl)-thio)ethyl)-thiourea.

A solution of 18.5 g (86.3 mmol) of 2-(((5-dimethylamino)methyl-2-furanyl)methyl)thio)ethanamine in 350 ml chloroform is additional dropwise with 12.22 ml (90.8 mmol) benzoyl-isothiocyanate at room temperature. After stirring for 30 minutes the solvents is evaporated and the raw product is purified by chromatography on silica gel in dichloromethane/methanol 15:1.

The oily residue as obtained by chromatography is crystallized by adding 80 ml ether. After stirring for 2 hours at room temperature the crystalline material is filtered, washed with ether (2×50 ml) and dried at 25° C./0.1 torr for 3 days to obtain 24.7 g of N-benzoyl-N'-(2-(((5-(dimethylamino)methyl-2-furanyl)methyl)thio)ethyl)-thiourea, m.p.=83°–85° C.

Found: C 57.21, H 6.18, N 11.08. Calc. for $C_{18}H_{23}N_3O_2S_2$: C 57.26, H 6.14, N 11.13.

EXAMPLE 2

N-(2-(((5-dimethylamino)methyl-2-furanyl-methyl)-thio)ethyl)-thiourea.

A mixture of 24.76 g (65.6 mmol) of N-benzoyl-N'-(2-(((5-(dimethylamino)methyl-2-furanyl)methyl)thio)ethyl)-thiourea and 5.6 g (40.5 mmol) of potassium carbonate in 160 ml ethanol and 100 ml water is heated under stirring at 65° C. An additional amount of 3.45 g (25 mmol) potassium carbonate is added after 30 and 75 minutes respectively. After 90 minutes the ethanol is eliminated by vacuum distillation. A reaction mixture is diluted with 200 ml 5% sodium carbonate and extracted with dichloromethane (3×250 ml). The organic compound is washed with 5% sodium carbonate (2×500 ml), dried over anhydrous magnesium sulfate and concentrated to a brown oil. After chromatography on 500 g silica gel in dichloromethane/methanol 9:1, 16.8 g of N-(2-(((5-(dimethylamino)methyl-2-furanyl)methyl)thio)ethylthiourea oil is obtained.

EXAMPLE 3

2-(2-(((5-(dimethylamino)methyl-2-furanyl)methyl)-thio)ethyl)-amino-4-phenylthiazole.

An ice cooled and stirred solution of 5.86 g (21.4 mmol) of N-(2-(((5-(dimethylamino)methyl-2-furanyl)-methyl)thio)ethyl)-thiourea in 50 ml methanol is quickly additioned with 4.28 g (21.4 mmol) of phenacyl bromide. The mixture is warmed to room temperature and kept under continuous stirring for an hour. The obtained residue after solvent evaporation is re-dissolved into 200 ml dichloromethane and subsequently washed with 5% sodium carbonate (2×100 ml) and a saturated solution of sodium chloride (1×100 ml). Concentrating the organic compound provides 7.9 g of an oil which is purified by chromatography on 400 g silica gel in dichloromethane/methanol 15:1. The collected material is re-dissolved into 40 ml ether. The filtered solution is vacuum concentrated obtaining, after drying at 35° C./0.4 torr for 30 hours, 5.9 g of 2-(2-(((5-(dimethylamino)methyl-2-furanyl)methyl)thio)ethyl)amino-4-phenyl-thiazole oil.

Found: C 60.82, H 6.32, N 11.17. Calc. for $C_{19}H_{23}N_3OS_2$: C 61.09, H 6.20, N 11.24.

EXAMPLE 4

In a similar way 2-(2-(((5-(dimethylamino)methyl-2-furanyl)methyl)thio)ethyl)amino-4-styryl-thiazole is prepared from N-(2(((5-(dimethylamino)methyl)-2-furanyl)methyl)thio)ethyl)-thiourea and 4-bromo-1-phenyl-1-buten-3-one (prepared according to D. V. C. Awang, S. Wolfe, Canad. J. Chemistry, 47, 706 (1969)). The oil is of orange colour, Rf=0.25 in dichloromethane/methanol 9:1.

Found: C 63.12, H 6.30, N 10.51. Calc. for $C_{21}H_{25}N_3OS_2$: C 63.16, H 6.40, N 10.41.

EXAMPLE 5

2-(2-(((5-(dimethylamino)methyl-2-furanyl)methyl)-thio)ethyl)amino-4-(4-biphenyl)-thiazole.

An ice cooled solution of 5.00 g (18.3 mmol) of N-(2-(((5-dimethylamino)methyl-2-furanyl)methyl)thio)ethyl)-thiourea in 100 ml tetrahydrofurane (THF) is additioned with 5.04 g (18.3 mmol) of 4-phenyl-phenacyl-bromide. The mixture is warmed to room temperature under continuous stirring for 1 hour. After removing the THF, the residue is dissolved into 200 ml dichloromethane and washed with 5% sodium carbonate (2×100 ml) and saturated sodium chloride. The organic compound gives 8.1 g of a solid which is re-dissolved into 250 ml ether. The insoluble material is removed by filtration, the filtrate is concentrated to a volume of about 20 ml and kept at −20° C. overnight. The crystal precipitate is removed by filtration and washed with ether (2×8 ml) at 0° C. Recrystallization from 150 ml ether provides, after drying at 30° C./0.5 torr for 65 hours, 3.27 g of 2-(2-(((5-(dimethylamino)methyl-2-furanyl)methyl)thio)ethyl)amino-4-(4-biphenyl)-thiazole. M.p.=70°–72° C.

Found: C 67.03, H 6.23, N 9.43. Calc. for $C_{25}H_{27}N_3OS_2$: C 66.78, H 6.05, N 9.34.

EXAMPLE 6

2-(2-(((5-(dimethylamino)methyl-2-furanyl)methyl)-thio)ethyl)-amino-4-(2-naphthyl)-thiazole.

Following the procedure of example 3, from a solution of 5.0 g (18.28 mmol) N-(2-(((5-(dimethylamino)-methyl-2-furanyl)methyl)thio)ethyl)-thiourea and 4.6 g (18.28 mmol) bromomethyl-2-naphthyl ketone (99%) in 90 ml tetrahydrofurane, 3.46 g 2-(2-(((5-(dimethylamino)methyl-2-furanyl)methyl)thio)ethyl)amino-4-(2-naphthyl)-thiazole was obtained. Red-brown oil, Rf=0.38 in dichloromethane/methanol 9:1.

Found: C 64.98, H 6.01, N 9.74. Calc. for $C_{23}H_{25}N_3OS_2$: C 65.21, H 5.95, N 9.92.

EXAMPLE 7

2-(2-(((5-(dimethylamino)methyl-2-furanyl)methyl)-thio)ethyl)-amino-4-(4-bromo)phenyl-thiazole.

Following the procedure of example 3, reaction of 6.53 g (23.91 mmol) N-(2-(((5-(dimethylamino)methyl-2-furanyl)methyl)thio)ethyl)thiourea with 6.64 g (23.91 mmol) 4-bromo-phenacyl-bromide in 115 ml THF gave 5.17 g 2-(2-(((5-(dimethylamino)methyl-2-furanyl)methyl)thio)ethyl)amino-4-(4-bromo)phenyl-thiazole. Red-brown oil, Rf=0.43 in dichloromethane/methanol 9:1.

Found: C 49.96, H 5.16, N 8.96. Calc. for $C_{19}H_{22}N_3OS_2Br$: C 50.43, H 4.90, N 9.28.

EXAMPLE 8

2-(2-(((5-(dimethylamino)methyl-2-furanyl)methyl)-thio)ethyl)-amino-4-(4-methoxy)phenyl-thiazole.

Similar to the procedure described in example 5, from a solution of 8.45 g (30.93 mmol) N-(2-(((5-dimethylamino)methyl-2-furanyl)methyl)thio)ethyl)-thiourea and 7.08 g (30.93 mmol) 4-methoxy-phenacylbromide in 140 ml tetrahydrofurane, 5.08 g 2-(2-(((5-(dimethylamino)methyl-2-furanyl)methyl)thio)ethyl)amino-4-(4-methoxy)phenyl-thiazole was obtained after crystallization from ether, m.p.=72°–74° C.

Found: C 59.54, H 6.25, N 10.32. Calc. for $C_{20}H_{25}N_3O_2S_2$: C 59.52, H 6.24, N 10.41.

EXAMPLE 9

2-(2-(((5-(dimethylamino)methyl-2-furanyl)methyl)-thio)ethyl)amino-4-(adamant-1-yl)-thiazole.

A solution of 6.06 g (22.18 mmol) N-(2-(((5-(dimethylamino)methyl-2-furanyl)methyl)thio)ethyl)thiourea in 90 ml ethanol to which was rapidly added 5.70 g (22.18 mmol) 1-adamantyl-bromo methyl-ketone was stirred at room temperature under a nitrogen atmosphere for 1 hour. Work-up and purification of the crude product according to the procedure described in example 3 gave 5.56 g 2-(2-(((5-(dimethylamino)methyl-2-furanyl)methyl)thio)ethyl)amino-4-adamant-1-yl)-thiazole. Yellow oil, Rf=0.44 in dichloromethane/methanol 9:1.

Found: C 64.04, H 7.84, N 9.45. Calc. for $C_{23}H_{33}N_3OS_2$: C 63.99, H 7.70, N 9.73.

EXAMPLE 10

2-(2-(((5-(dimethylamino)methyl-2-furanyl)methyl)-thio)ethyl)amino-4-hexyl-thiazole.

Similar to the procedure of example 9, from a solution of 7.26 g (26.57 mmol) N-(2-(((5-dimethylamino)methyl-2-furanyl)methyl)thio)ethyl)-thiourea and 5.50 g (26.57 mmol) 1-bromo-2-octanone in 100 ml ethanol at room temperature was obtained 5.11 g 2-(2-(((5-(dimethylamino)methyl-2-furanyl)methyl)thio)ethyl)amino-4-hexyl-thiazole. Yellow oil, Rf=0.38 in dichloromethane/methanol 15:1.

Found: C 59.89, H 8.09, N 10.97. Calc. for $C_{19}H_{31}N_3OS_2$: C 59.80, H 8.18, N 11.01.

EXAMPLE 11

2-(2-(((5-(dimethylamino)methyl-2-furanyl)methyl)-thio)ethyl)amino-4-(4-biphenyl)methyl-thiazole.

Similar to the procedure of example 9, 5.07 g 2-(2-(((5-(dimethylamino)methyl-2-furanyl)methyl)thio)ethyl)amino-4-(4-biphenyl)methyl-thiazole was obtained by mixing a solution of 6.43 g (23.51 mmol) N-(2-(((5-(dimethylamino)methyl-2-furanyl)methyl)thio)ethyl)-thiourea in 60 ml ethanol and 6.80 g (23.51 mmol) bromomethyl-(4-biphenyl)methyl ketone in 20 ml ethanol and 15 ml tetrahydrofurane. Red-brown oil.

Found: C 67.01, H 6.52, N 8.85. Calc. for $C_{26}H_{29}N_3OS_2$: C 67.35, H 6.30, N 9.06.

EXAMPLE 12

2-(2-(((5-(dimethylamino)methyl-2-furanyl)methyl)-thio)ethyl)amino-4-(3,4-ethylenedioxy)phenyl-thiazole.

Similar to the procedure of example 9, from a mixture of 5.86 g (21.43 mmol) N-(2-(((5-(dimethylamino)methyl-2-furanyl)methyl)thio)ethyl)thiourea in 60 ml ethanol and 5.51 g (21.43 mmol) bromomethyl-(3,4-ethylenedioxy)phenylketone in 45 ml tetrahydrofurane, 5.07 g 2-(2-(((5-(dimethylamino)methyl-2-furanyl)methyl)thio)ethyl)amino-4-(3,4-ethylenedioxy)-phenyl-thiazole was isolated. Red-brown oil, Rf=0.25 in dichloromethane/methanol 9:1.

Found: C 58.17, H 6.08, N 9.48. Calc. for $C_{21}H_{25}N_3O_3S_2$: C 58.44, H 5.83, N 9.73.

EXAMPLE 13

2-(2-(((5-(dimethylamino)methyl-2-furanyl)methyl)-thio)ethyl)amino-4-(4-phenoxy)phenyl-thiazole.

Similar to the procedure of example 9, 6.03 g of 2-(2-(((5-(dimethylamino)methyl-2-furanyl)methyl)thio)ethyl)amino-4-(4-phenoxy)phenyl-thiazole was prepared by addition of 6.04 g solid (24.48 mmol) chloromethyl-(4-phenoxy)phenyl-ketone (prepared from biphenylether and chloro-acetylchloride by a Friedel-Crafts acetylation) to a stirred solution of 6.69 g (24.48 mmol) N-(2-(((5-(dimethylamino)methyl-2-furanyl)methyl)thio)ethyl)thiourea in 80 ml ethanol. Red-brown oil, Rf.=0.32 in dichloromethane/methanol 9:1.

Found: C 64.32, H 5.97, N 8.91. Calc. for $C_{25}H_{27}N_3O_2S_2$: C 64.48, H 5.84, N 9.02.

Pharmacological tests

Experimental tests show that the compounds according to the present invention have pharmacological properties for therapeutic application in some pathological states. The utility of the 2-amino-thiazole derivatives is documented in the tests hereinafter referred, which show antagonistic properties to the histamine $H_2$ receptors and an ability to reduce for an extended time period the gastric acid secretion in experimental tests on animals.

This pharmacotherapeutic effect was obtained with dosages and administration methods which have not resulted in significant toxic effects.

The antagonistic effect to the histamine $H_2$ receptors and the activity on the gastric secretion have been tested by comparing the 2-amino-thiazole derivatives of the present invention with Cimetidine and Ranitidine, the anti-$H_2$ properties of which are known. (Takeda M. and coll., Arzneim.-Forsch./Drug Res. 32 (II), No. 7, 734, 1982; Toson G. and coll., Il Farmaco, Ed. Pr., 38, (9), 352, 1983.)

The preparations were a solution of the substances in 2.5% citric acid for the "in vitro" test and 5% citric acid for the "in vivo" test respectively. Citric acid was diluted in normal physiologic saline at neutral pH.

Antagonistic activity to the histamine $H_2$ receptors

This activity was evaluated "in vitro" by carrying out tests on insulated atrium auricolas of Guinea pig heart. Indeed it is known (Daly M. J., Br. J. Pharmac., 72, 49, 1982) that substances such as Cimetidine and Ranitidine competitively antagonize a histamine induced increase of the contraction frequency of the insulated atrium. Metering was carried out by placing the preparation into a vessel containing a Ringer-Locke solution wherein pure oxygen was bubbling, at a temperature of 37° C. A response of the organ "in vitro" was first established at cumulative histamine doses of $2.5 \cdot 10^{-7}$, $5 \cdot 10^{-7}$, $10^{-6}$, $5 \cdot 10^{-6}$, $10^{-5}$ M/L. After obtaining two constant lines with histamine at a time interval of one hour from one another, the substances under test were added to the bath and after a 30 minutes contact with the preparation, a new histamine response line in the presence of the substance under test was drawn. The activity was tested at various concentrations of the new compounds ($10^{-5}$, $10^{-6}$, $10^{-7}$ and in one case $10^{-8}$ M/L).

The 2-amino-thiazole derivatives show in this "in vitro" test, a considerable antagonistic action to the histamine $H_2$ receptors and the used doses and their % activity are reported in table I.

Activity on gastric secretion

The ability of the compounds according to the present invention to inhibit the gastric secretion was studied "in vivo" both by evaluating the volume reduction of gastric juice, and by measuring the total acidity of same after administration of the substances under test according to the Takeda method (see the aforementioned literature).

To this end, tests have been made on male Wistar rats of an average weight of 200 g. The animals, 10 for each substance, were placed into individual cages provided with ground grating in order to avoid coprophagy, without food but with free access to water for 24 hours before test. The treatment per os was made one hour before tieing the pylorus under ether anaesthesia and operating according to Shay (Shay H. and coll., gastroenterology, 4, 43–61, 1945). Four hours later the animals were sacrificed and the gastric juice was collected, of which the volume expressed in ml and the total acidity expressed in mEq was measured. The gastric juice (0.5 ) was titrated with 0.1N NaOH to pH 7 to determine the acid concentration. The total acidity was then calculated as the product of the total volume of gastric juice by the acid concentration. The 2-amino-thiazole derivatives (table II) show a high activity both in reducing the gastric juice volume and inhibiting the total acidity. Such an activity, surprisingly, is also maintained in time, in a decreasing way up to 36 hours.

Tables III and IV show the results obtained by administrating the compounds 3-6-12-24-36 hours before tieing pylorus.

$DE_{50}$

In order to have a summary of the activity of the new derivatives in comparison with known anti-$H_2$ substances (Ranitidine, Cimetidine), the $DE_{50}$ calculated by the parameter of the gastric juice total acidity after administration of the products under test are referred in table V.

Toxicity $DL_{50}$ was determined after administering once per os the compounds according to examples 1, 3, 4, 5, 6, 13 in comparison with Cimetidine and Ranitidine, in albine male Swiss mouse of an average weight of 26 g and in Wistar rat of average weight of 150 g. The animals were kept under observation by checking mortality and possible pain signs for 15 days from start of test. In table VI the values of $DL_{50}$ (mg/kg) are reported.

TABLE I

| | | Antagonizing activity of 2-amino-thiazole derivatives to histamine $H_2$ receptors | | | | |
|---|---|---|---|---|---|---|
| | Dose | Antagonizing activity Histamine concentration (M/L) | | | | |
| Compounds | M/L | $2,5 \cdot 10^{-7}$ | $5 \cdot 10^{-7}$ | $1 \cdot 10^{-6}$ | $5 \cdot 10^{-6}$ | $1 \cdot 10^{-5}$ |
| Carrier | — | 0% | 0% | 0% | 0% | 0% |
| Example No. 1 | $1 \cdot 10^{-5}$ | 100% | 100% | 100% | 100% | 100% |
| " | $1 \cdot 10^{-6}$ | 100% | 90% | 80% | 60% | 50% |
| " | $1 \cdot 10^{-7}$ | 90% | 85% | 65% | 35% | 20% |
| Example No. 3 | $1 \cdot 10^{-5}$ | 100% | 100% | 100% | 100% | 95% |
| " | $1 \cdot 10^{-6}$ | 100% | 100% | 85% | 70% | 52% |
| " | $1 \cdot 10^{-7}$ | 85% | 70% | 50% | 30% | 20% |
| Example No. 4 | $1 \cdot 10^{-5}$ | 100% | 100% | 100% | 100% | 93% |
| " | $1 \cdot 10^{-6}$ | 100% | 100% | 70% | 60% | 38% |
| " | $1 \cdot 10^{-7}$ | 90% | 70% | 45% | 35% | 20% |
| Example No. 5 | $1 \cdot 10^{-5}$ | 100% | 100% | 100% | 100% | 100% |
| " | $1 \cdot 10^{-6}$ | 100% | 90% | 70% | 60% | 45% |
| " | $1 \cdot 10^{-7}$ | 95% | 85% | 65% | 40% | 25% |
| Example No. 6 | $1 \cdot 10^{-5}$ | 100% | 100% | 100% | 90% | 90% |
| " | $1 \cdot 10^{-6}$ | 100% | 100% | 90% | 70% | 40% |
| " | $1 \cdot 10^{-7}$ | 95% | 95% | 70% | 50% | 35% |
| " | $1 \cdot 10^{-8}$ | 95% | 85% | 70% | 50% | 15% |
| Example No. 13 | $1 \cdot 10^{-5}$ | 100% | 100% | 95% | 90% | 90% |
| " | $1 \cdot 10^{-6}$ | 90% | 90% | 80% | 65% | 38% |
| " | $1 \cdot 10^{-7}$ | 90% | 70% | 50% | 30% | 40% |
| Cimetidine | $1 \cdot 10^{-5}$ | 100% | 100% | 100% | 50% | 28% |
| " | $1 \cdot 10^{-6}$ | 100% | 90% | 90% | 40% | 10% |
| " | $1 \cdot 10^{-7}$ | 80% | 80% | 45% | 22% | 0% |
| Ranitidine | $1 \cdot 10^{-5}$ | 100% | 100% | 100% | 95% | 90% |
| " | $1 \cdot 10^{-6}$ | 100% | 100% | 97% | 67% | 36% |
| " | $1 \cdot 10^{-7}$ | 85% | 70% | 45% | 25% | 2% |

TABLE II

| | "In vivo" activity of 2-amino-thiazole derivatives on gastric secretion. Oral route treatment 1 hour before pilorus tieing. | | | | |
|---|---|---|---|---|---|
| Compounds | Dose mg/kg | Volume gastric juice secretion ml/4 hours | Variation % | Total acidity gastric juice secretion mEq/4 hours | Variation % |
| Carrier | — | 5,5 | — | 0,18 | — |
| Example No. 1 | 0,1 | 5,0 | −9 | 0,16 | −11 |
| " | 1,0 | 3,8 | −31 | 0,11 | −39 |
| " | 5,0 | 3,6 | −35 | 0,09 | −50 |
| " | 10,0 | 3,5 | −36 | 0,07 | −61 |
| " | 20,0 | 3,2 | −42 | 0,06 | −72 |
| Example No. 3 | 0,1 | 5,2 | −5 | 0,15 | −17 |
| " | 1,0 | 4,1 | −25 | 0,10 | −44 |
| " | 5,0 | 3,5 | −36 | 0,08 | −55 |
| " | 10,0 | 3,2 | −42 | 0,06 | −67 |
| " | 20,0 | 3,0 | −45 | 0,04 | −78 |
| Example No. 4 | 0,1 | 5,0 | −9 | 0,16 | −11 |
| " | 1,0 | 4,1 | −25 | 0,11 | −39 |
| " | 5,0 | 3,7 | −33 | 0,09 | −50 |

TABLE II-continued

"In vivo" activity of 2-amino-thiazole derivatives on gastric secretion.
Oral route treatment 1 hour before pilorus tieing.

| Compounds | Dose mg/kg | Volume gastric juice secretion ml/4 hours | Variation % | Total acidity gastric juice secretion mEq/4 hours | Variation % |
|---|---|---|---|---|---|
| " | 10,0 | 3,5 | −36 | 0,06 | −67 |
| " | 20,0 | 3,3 | −40 | 0,05 | −72 |
| Example No. 5 | 0,1 | 5,1 | −7 | 0,14 | −22 |
| " | 1,0 | 4,1 | −25 | 0,10 | −44 |
| " | 5,0 | 3,7 | −33 | 0,07 | −61 |
| " | 10,0 | 3,5 | −36 | 0,05 | −72 |
| " | 20,0 | 3,0 | −45 | 0,03 | −83 |
| Example No. 6 | 0,1 | 4,9 | −11 | 0,14 | −22 |
| " | 1,0 | 4,1 | −25 | 0,11 | −39 |
| " | 5,0 | 3,7 | −33 | 0,08 | −55 |
| " | 10,0 | 3,4 | −38 | 0,06 | −67 |
| " | 20,0 | 3,3 | −40 | 0,04 | −78 |
| Example No. 13 | 0,1 | 5,0 | −9 | 0,14 | −22 |
| " | 1,0 | 4,4 | −20 | 0,12 | −33 |
| " | 5,0 | 3,9 | −29 | 0,08 | −55 |
| " | 10,0 | 3,5 | −36 | 0,06 | −67 |
| " | 20,0 | 3,4 | −38 | 0,05 | −72 |
| Cimetidine | 0,1 | 5,5 | 0 | 0,18 | 0 |
| " | 1,0 | 5,4 | −2 | 0,18 | 0 |
| " | 5,0 | 5,0 | −9 | 0,16 | −11 |
| " | 10,0 | 4,7 | −15 | 0,15 | −17 |
| " | 20,0 | 4,5 | −18 | 0,12 | −33 |
| Ranitidine | 0,1 | 5,1 | −7 | 0,16 | −11 |
| " | 1,0 | 4,2 | −24 | 0,12 | −33 |
| " | 5,0 | 3,8 | −31 | 0,11 | −39 |
| " | 10,0 | 3,6 | −35 | 0,07 | −61 |
| " | 20,0 | 3,4 | −38 | 0,07 | −61 |

TABLE III

"In vivo" activity of 2-amino-thiazole derivatives on gastric secretion.
Oral route treatment 3 hours before pilorus tieing.

| Compounds | Dose ml/kg | Volume gastric juice secretion ml/4 hours | Variation % | Total acidity gastric juice secretion mEq/4 hours | Variation % |
|---|---|---|---|---|---|
| Carrier | — | 5,4 | — | 0,18 | — |
| Example No. 1 | 0,1 | 5,1 | −6 | 0,16 | −11 |
| " | 1,0 | 4,7 | −13 | 0,13 | −18 |
| " | 10,0 | 3,9 | −28 | 0,09 | −50 |
| " | 20,0 | 3,7 | −31 | 0,08 | −55 |
| Example No. 3 | 0,1 | 5,2 | −4 | 0,17 | −6 |
| " | 1,0 | 4,5 | −17 | 0,14 | −22 |
| " | 10,0 | 3,8 | −30 | 0,10 | −44 |
| " | 20,0 | 3,4 | −37 | 0,07 | −61 |
| Example No. 4 | 0,1 | 5,0 | −7 | 0,16 | −11 |
| " | 1,0 | 4,7 | −13 | 0,14 | −22 |
| " | 10,0 | 4,0 | −26 | 0,11 | −39 |
| " | 20,0 | 3,8 | −30 | 0,09 | −50 |
| Example No. 5 | 0,1 | 4,7 | −13 | 0,11 | −39 |
| " | 1,0 | 4,0 | −26 | 0,09 | −50 |
| " | 10,0 | 3,6 | −33 | 0,06 | −67 |
| " | 20,0 | 3,2 | −41 | 0,05 | −72 |
| Example No. 6 | 0,1 | 5,0 | −7 | 0,15 | −17 |
| " | 1,0 | 4,8 | −11 | 0,10 | −44 |
| " | 10,0 | 4,2 | −22 | 0,07 | −61 |
| " | 20,0 | 2,4 | −55 | 0,06 | −67 |
| Example No. 13 | 0,1 | 5,1 | −5 | 0,16 | −11 |
| " | 1,0 | 4,9 | −9 | 0,12 | −33 |
| " | 10,0 | 4,3 | −20 | 0,08 | −55 |
| " | 20,0 | 3,9 | −28 | 0,07 | −61 |
| Cimetidine | 0,1 | 5,5 | 0 | 0,18 | 0 |
| " | 1,0 | 4,8 | −11 | 0,16 | −11 |
| " | 10,0 | 5,2 | −5 | 0,15 | −17 |
| " | 20,0 | 5,0 | −7 | 0,14 | −22 |
| Ranitidine | 0,1 | 5,3 | −4 | 0,16 | −11 |
| " | 1,0 | 4,7 | −13 | 0,16 | −11 |
| " | 10,0 | 4,5 | −17 | 0,14 | −22 |
| " | 20,0 | 4,0 | −26 | 0,13 | −28 |

TABLE IV

"In vivo" activity of 2-amino-thiazole derivatives on the gastric secretion.
Oral route treatment 6-12-24-36 hours before pilorus tieing at a 20 mg/kg dose.

| Compounds | Hours | Volume gastric juice secretion ml/4 hours | Variation % | Total acidity gastric juice secretion mEq/4 hours | Variation % |
|---|---|---|---|---|---|
| Carrier | 6 | 5,3 | — | 0,17 | — |
| Example No. 1 | " | 4,1 | −23 | 0,08 | −53 |
| Example No. 3 | " | 4,0 | −24 | 0,07 | −59 |
| Example No. 4 | " | 3,9 | −26 | 0,09 | −47 |
| Example No. 5 | " | 3,7 | −30 | 0,08 | −53 |
| Example No. 6 | " | 3,0 | −43 | 0,05 | −70 |
| Example No. 13 | " | 3,9 | −26 | 0,09 | −47 |
| Ranitidine | " | 4,8 | −9 | 0,12 | −29 |
| Carrier | 12 | 5,1 | — | 0,15 | — |
| Example No. 1 | " | 4,0 | −21 | 0,09 | −40 |
| Example No. 3 | " | 4,1 | −20 | 0,10 | −33 |
| Example No. 4 | " | 4,0 | −21 | 0,08 | −47 |
| Example No. 5 | " | 3,8 | −25 | 0,08 | −47 |
| Example No. 6 | " | 2,9 | −37 | 0,04 | −73 |
| Example No. 13 | " | 3,9 | −23 | 0,09 | −40 |
| Ranitidine | " | 4,9 | −4 | 0,16 | +6 |
| Carrier | 24 | 5,6 | — | 0,17 | — |
| Example No. 1 | " | 5,0 | −11 | 0,13 | −23 |
| Example No. 3 | " | 4,8 | −14 | 0,12 | −29 |
| Example No. 4 | " | 4,9 | −13 | 0,14 | −18 |
| Example No. 5 | " | 4,9 | −13 | 0,13 | −23 |
| Example No. 6 | " | 4,5 | −20 | 0,12 | −29 |
| Example No. 13 | " | 4,7 | −16 | 0,13 | −23 |
| Ranitidine | " | 5,3 | −5 | 0,17 | 0 |
| Carrier | 36 | 5,6 | — | 0,16 | — |
| Example No. 1 | " | 5,2 | −7 | 0,14 | −12 |
| Example No. 3 | " | 5,0 | −11 | 0,15 | −6 |
| Example No. 4 | " | 5,3 | −5 | 0,14 | −12 |
| Example No. 5 | " | 4,4 | −21 | 0,13 | −19 |
| Example No. 6 | " | 5,0 | −11 | 0,12 | −25 |
| Example No. 13 | " | 5,1 | −9 | 0,15 | −6 |
| Ranitidine | " | 5,4 | −3 | 0,16 | 0 |

TABLE V $DE_{50}$ in rat calculated on total acidity (mEq/4 hours) after administration per os of 2-amino-thiazole derivatives 1 hour before pilorus tieing.

| Compounds | $DE_{50}$ mg/Kg |
|---|---|
| Example No. 1 | 3,4 |
| Example No. 3 | 2,2 |
| Example No. 4 | 3,2 |
| Example No. 5 | 1,6 |
| Example No. 6 | 1,8 |
| Example No. 13 | 2,6 |
| Cimetidine | 30,0 |
| Ranitidine | 5,2 |

TABLE VI

Acute toxicity in mouse and rat of 2-amino-thiazole derivatives.

| Compounds | $DL_{50}$ (mg/kg/os) Mouse | Rat |
|---|---|---|
| Example No. 1 | 750 | 1.000 |
| Example No. 3 | 550 | 900 |
| Example No. 4 | 2.900 | 3.000 |
| Example No. 5 | 2.300 | 3.300 |
| Example No. 6 | 2.100 | 2.800 |
| Example No. 13 | 3.000 | >3.000 |
| Cimetidine | 2.600 | 5.000* |
| Ranitidine | 1.600 | 2.000 |

*Value known from: Brimbelcombe R. W., J. Int. Med. Res., 3,86,1975.

The compounds according to examples 1, 3, 4, 5, 6, 13 show to have an interesting ability to antagonize "in vitro" the histamine $H_2$ receptors and to reduce the gastric acid secretion. The $DE_{50}$ values referred in table V evidence that the compounds according to the present invention are more powerful than Cimetidine and Ranitidine in inhibiting the total acidity and that their activity is extended in time (table III-IV) both on the volume and the acidity of the gastric juice, which effect is practically absent in the comparison drugs.

The low toxicity (table VI) of the new derivatives provide them with a high therapeutic index. The acute toxicity values are in fact by several factors higher than the pharmacologically active doses. With the doses and methods used and described in the above tests, the administration to healthy animals has not resulted in a long or short term mortality, nor apparent signs of toxic effects. The data referred in tables I-VI evidence the utility of the compounds according to the present invention for the treatment of disturbances due to hyperstimulation of histamine $H_2$ receptors and to gastric acid secretion as caused, for example, by ulcer of the gastrointestinal tract.

The compounds of general formula (I) can be administered to patients both orally and parenterally in doses from 1 mg to 200 mg, once or twice a day. To this end the compounds according to the present invention can be conventionally formulated for oral or parenteral preparations in order to obtain absorption and distribution of the drug in the animal or human circulatory system.

I claim:

1. Compound of formula (I)

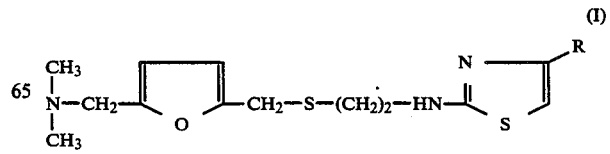

wherein R is $C_1$ to $C_6$ alkyl, naphthyl, adamantyl, a diphenyl ether group, phenyl or a substituted phenyl which is monosubstituted with halogen, lower.alkoxy, lower.alkylaryl, styryl, ethylene dioxyphenoxy or phenyl- and salts, N- or S-oxides or hydrate thereof.

2. Compound according to claim 1, wherein R is a hexyl group.

3. Compound according to claim 1, wherein R is a -(4-bromo)phenyl group.

4. Compound according to claim 1, wherein R is a -(4-methoxy)phenyl group.

5. Compound according to claim 1, wherein R is a -(3,4-ethylenedioxy)phenyl group.

6. Compound according to claim 1, wherein R is a -(4-biphenyl)methyl group.

7. A pharmaceutical composition for treating a condition mediated through gastric acid secretion comprising a pharmaceutically effective amount of a compound of formula (I) as recited in claim 1 and a pharmaceutically acceptable carrier or diluent.

8. A method for treating a condition mediated through gastric acid secretion comprising administering to the patients an amount of a compound of formula (I) as recited in claim 1 therapeutically effective to relieve said condition.

* * * * *